United States Patent
Muhonen et al.

(10) Patent No.: US 11,289,846 B1
(45) Date of Patent: Mar. 29, 2022

(54) IV POLE POWER PLUG SUPPORT DEVICE

(71) Applicants: Kimberly Ann Muhonen, Buffalo, MN (US); Sean Carroll, Pasadena, MN (US)

(72) Inventors: Kimberly Ann Muhonen, Buffalo, MN (US); Sean Carroll, Pasadena, MN (US)

(*) Notice: Subject to any disclaimer, the term of this patent is extended or adjusted under 35 U.S.C. 154(b) by 76 days.

(21) Appl. No.: 16/001,173

(22) Filed: Jun. 6, 2018

Related U.S. Application Data

(60) Provisional application No. 62/604,119, filed on Jun. 24, 2017.

(51) Int. Cl.
| | | |
|---|---|---|
| *H01R 13/516* | (2006.01) | |
| *A61M 5/14* | (2006.01) | |
| *H01R 13/405* | (2006.01) | |

(52) U.S. Cl.
CPC ......... *H01R 13/516* (2013.01); *A61M 5/1415* (2013.01); *H01R 13/405* (2013.01)

(58) Field of Classification Search
CPC .............. A61M 5/1414; A61M 5/1415; A61M 5/1417; A61M 5/1418; H01R 13/516; H01R 13/60; H01R 13/73; F16M 13/02; G09F 2007/1804
See application file for complete search history.

(56) References Cited

U.S. PATENT DOCUMENTS

| | | | | |
|---|---|---|---|---|
| 3,318,457 A | * | 5/1967 | Krasnoff | A61M 5/1415 211/74 |
| 3,722,843 A | * | 3/1973 | Enckler | A47F 5/0823 248/300 |
| 4,346,957 A | * | 8/1982 | Fukao | H01R 13/60 439/529 |
| 4,921,444 A | * | 5/1990 | Cama | H01R 13/60 439/528 |
| 5,188,327 A | * | 2/1993 | White | A61G 7/0503 248/231.81 |
| 5,478,041 A | * | 12/1995 | Mayne | A45B 11/00 248/231.51 |
| 5,489,075 A | * | 2/1996 | Ible | A61J 9/0692 24/298 |
| 6,126,129 A | * | 10/2000 | Herron | A61M 5/1417 222/105 |
| 9,345,353 B2 | * | 5/2016 | Forbes | G09F 21/04 |
| 9,551,454 B2 | * | 1/2017 | Lipke | H02J 7/0044 |
| 10,159,783 B2 | * | 12/2018 | Kluttz | A61M 5/1418 |
| 2013/0306543 A1 | * | 11/2013 | Beisser | A61M 5/1418 210/321.6 |

* cited by examiner

*Primary Examiner* — Felix O Figueroa
(74) *Attorney, Agent, or Firm* — Stinson LLP

(57) ABSTRACT

An IV pole power plug support device for preventing an power plug and cord from dangling on a floor. The IV pole power plug support device includes a securement assembly adapted to be removably engaged about an IV pole; and a power plug holder in communication with the securement assembly.

18 Claims, 6 Drawing Sheets ained in the claims

IV POLE POWER PLUG SUPPORT DEVICE

CROSS-REFERENCE TO RELATED APPLICATIONS

The present application claims priority to the provisional application Ser. No. 62/604,119 filed on Jun. 24, 2017, the disclosure of which is expressly incorporated by reference herein in its entirety.

BACKGROUND OF THE INVENTION

Field of the Invention

The present invention relates to power plug holders and more particularly pertains to a new IV (intravenous) pole power plug support device for preventing a power plug and cord from dangling on a floor.

Description of the Prior Art

The use of power plug holders is known in the prior art. More specifically, power plug holders heretofore devised and utilized are known to consist basically of familiar, expected and obvious structural configurations, notwithstanding the myriad of designs encompassed by the crowded prior art which have been developed for the fulfillment of countless objectives and requirements.

The prior art includes clamps having a screw threaded through the clamp to secure the clamp to a pole with the clamps supporting an array of objects includes brackets and trays. While these devices fulfill their respective, particular objectives and requirements, the aforementioned patents do not disclose a new IV pole power plug support device.

SUMMARY OF THE INVENTION

The general purpose of the present invention, which will be described subsequently in greater detail, is to provide a new IV pole power plug support device which has many of the advantages of the power plug holders mentioned heretofore and many novel features that result in a new IV pole power plug support device which is not anticipated, rendered obvious, suggested, or even implied by any of the prior art power plug holders, either alone or in any combination thereof. The present invention includes a securement assembly adapted to be removably engaged about an IV pole; and a power plug holder in communication with the securement assembly. None of the prior art includes the combination of the elements of the present invention.

There has thus been outlined, rather broadly, the more important features of the IV pole power plug support device in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new IV pole power plug support device which has many of the advantages of the power plug holders mentioned heretofore and many novel features that result in a new IV pole power plug support device which is not anticipated, rendered obvious, suggested, or even implied by any of the prior art power plug holders, either alone or in any combination thereof.

Still another object of the present invention is to provide a new IV pole power plug support device for preventing an power plug and cord from dangling on a floor.

Still yet another object of the present invention is to provide a new IV pole power plug support device that supports the power plug and cord upon an IV pole so that it doesn't get in the way of the wheels of the pole as a user moves the IV pole upon a floor.

Even still another object of the present invention is to provide a new IV pole power plug support device that doesn't get in the way of a patient who is trying to maneuver the IV pole upon a floor and may trip upon the power plug and cord.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
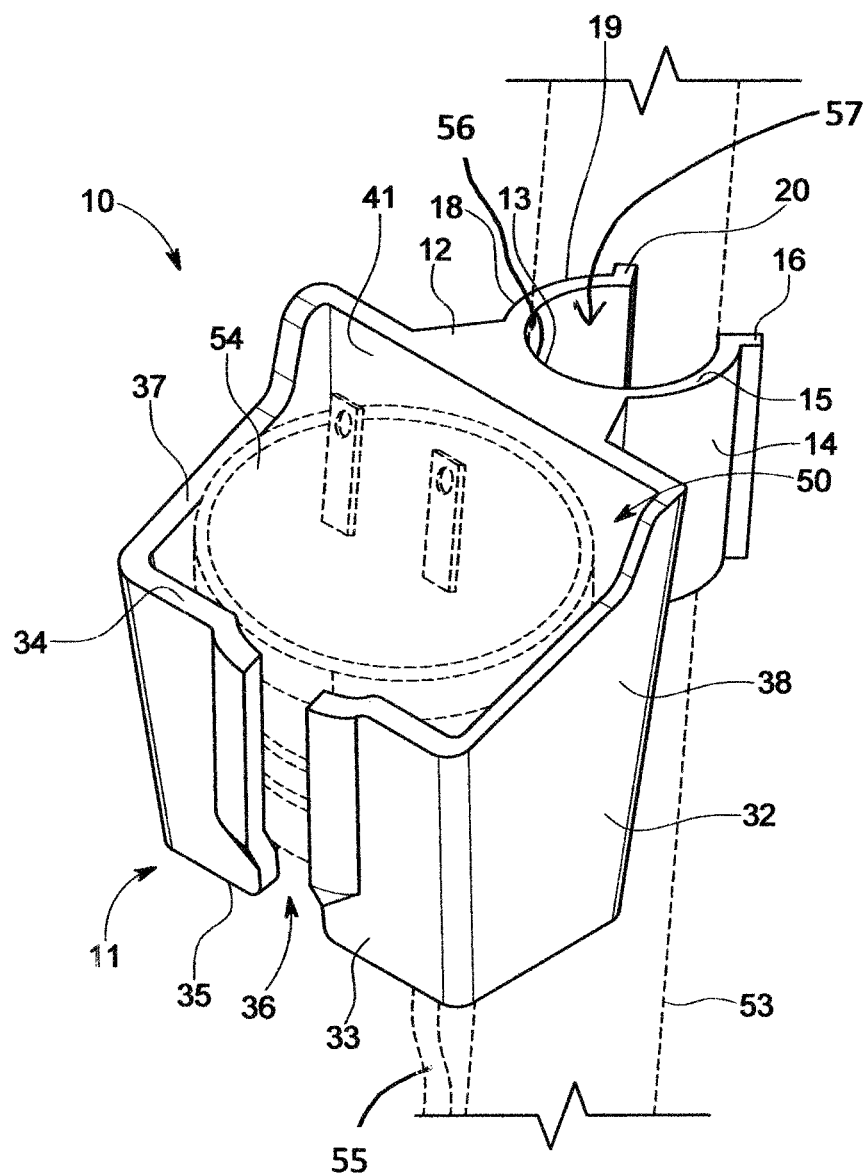
FIG. 1 is a top perspective view of a new IV pole power plug support device mounted to a pole.

With reference now to the drawings, and in particular to FIGS. 1 through 6 thereof, a new IV pole power plug support device embodying the principles and concepts of the present invention and generally designated by the reference numeral 10 will be described.

As best illustrated in FIGS. 1 through 6, the IV pole power plug support device 10 generally comprises a securement assembly 11 adapted to be removably engaged about an IV pole 53; and a power plug holder 32 in communication with the securement assembly 11.

The power plug holder 32 has opposed side walls 37, 38, a bottom wall 39 having an opening 40 disposed therethrough, a front wall 33 having top and bottom edges 34, 35 and an opening 36 disposed therethrough and through the top and bottom edges 34, 35 and being in fluid communication with the opening 40 through the bottom wall 39 for receiving a power cord 55 therethrough, and also has a cavity 50 disposed therein for holding a power plug 54. The front wall 33 has side edge portions 51, 52 which line the opening 36 through the front wall 33 and which are bowed outwardly to accommodate any shape and size of the power plug 54 held in the cavity 50.

The securement assembly 11 has a base 12 which is integral to the plug holder 32 and has an outer side 13. The securement assembly 11 also includes a pair of extensions 14, 18 extending outwardly from the outer side 13 of the base 12 and form a pole receiving and engaging slot 57 therebetween. Each of the extensions 14, 18 has a main portion 15, 19 and an end portion 16, 20. The main portions 15, 19 are laterally curved towards each other and the end portions 16, 20 are angled away from each other with each main portion 15, 19 with a non-slip material 56 conventionally attached to the securement assembly 11 and disposed in the pole receiving and engaging slot 57 to prevent the securement assembly 11 from slipping upon the pole 53.

Figure 2:
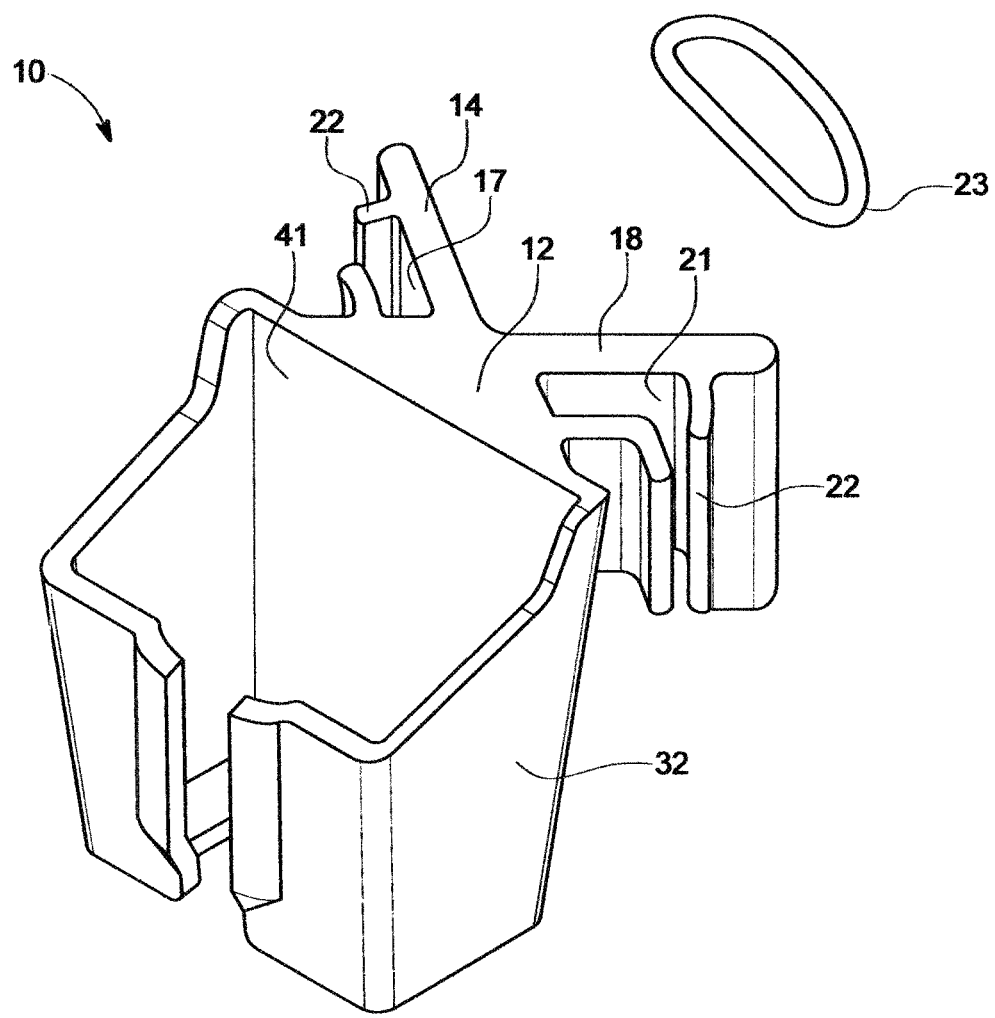
FIG. 2 is a top perspective view of a second embodiment of the present invention mounted about a pole.

As a second embodiment as shown in FIG. 2, each of the extensions 14, 18 has an outer side 17, 21 with a flange 22 disposed upon the outer side 17, 21 of the respective extension 14, 18. The securement assembly 11 further includes an elastic band 23 which is removably secured about the flanges 22 and adapted to be secured about the pole 53 to secure the IV pole power plug support device 10 to the pole 53.

Figure 3:
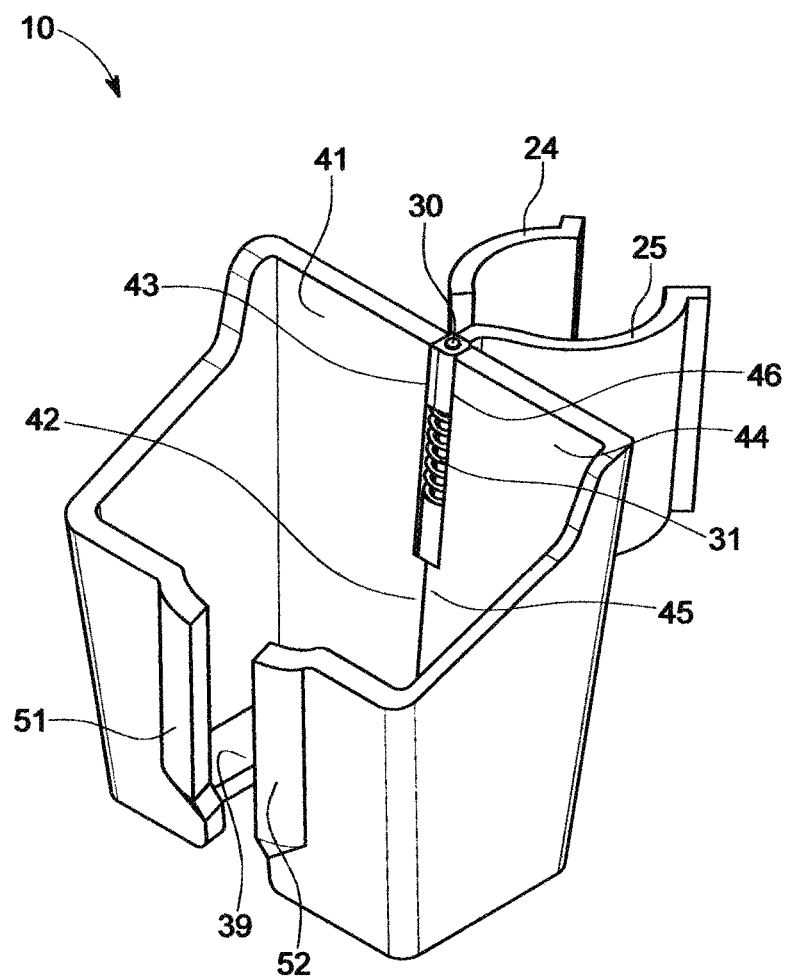
FIG. 3 is a top perspective view of a third embodiment of the present invention.
Figure 4:
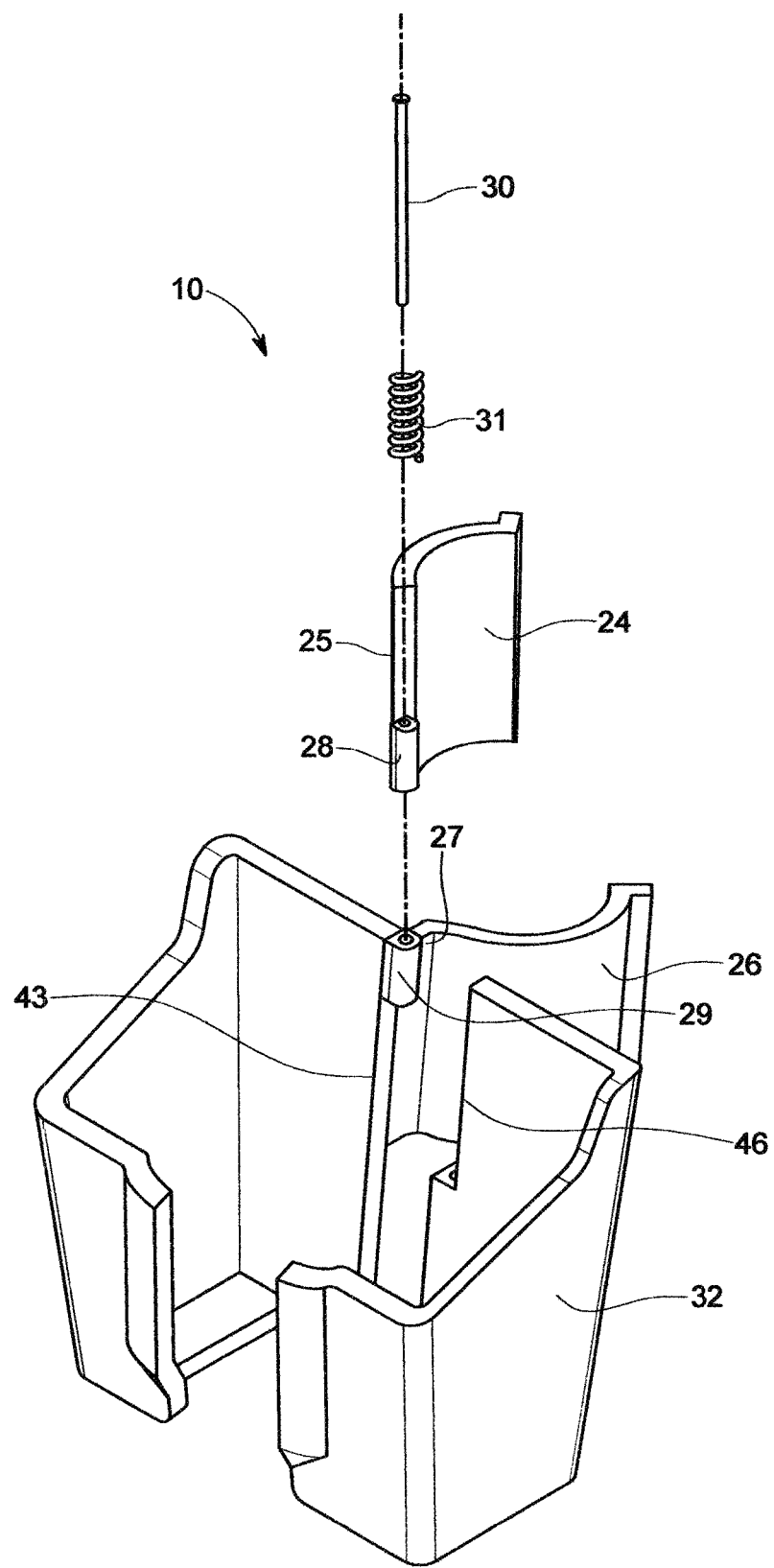
FIG. 4 is an exploded top perspective view of the third embodiment of the present invention.

As a third embodiment as illustrated in FIGS. 3 & 4, the securement assembly 11 includes a pair of clamping members 24, 26 spaced apart with each having a length and a proximate end edge 25, 27. The securement assembly 11 also includes tubular connectors 28, 29 each of which is conventionally coupled to the proximate end edge 25, 27 of a respective clamping member 24, 26. The clamping members 24, 26 are longitudinally curved towards one another. The securement assembly 11 further includes a pin 30 inserted through the tubular connectors 28, 29 and also includes a biased element 31 conventionally disposed about the pin 30 and engaged to the tubular connectors 28, 29 to engagably bias and secure the clamping members 24, 26 about the pole 53. The tubular connectors 28, 29 are hollow and each have a longitudinal axis which is arranged parallel to the proximate end edge 25, 27 of a respective clamping member 24, 26. The plug holder 32 includes a back wall 41 having a back side 49.

The plug holder 32 also includes support members 47, 48 spaced apart and integral to the back side 49 of the back wall 41 with the pin 30 being inserted in the support members 47, 48 to interconnect the clamping members 24, 26 to the plug holder 32. The tubular connectors 28, 29 are disposed between and are longitudinally aligned with the support members 47, 48.

Figure 5:
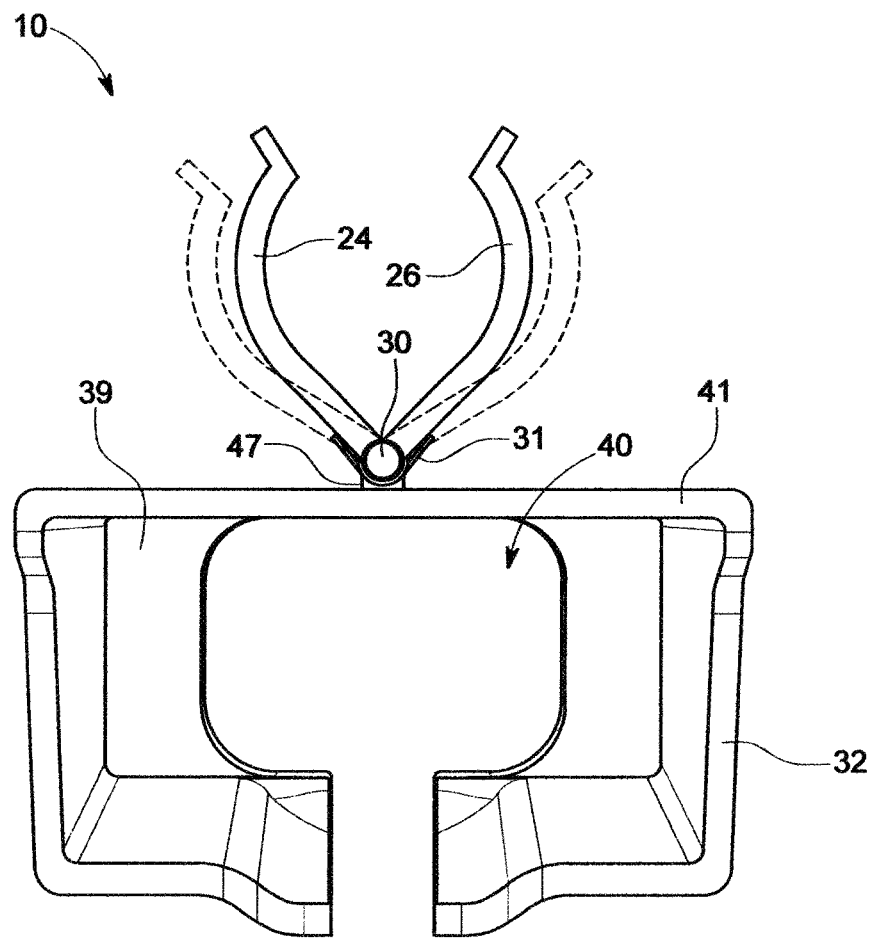
FIG. 5 is a top plan view of a fourth embodiment of the present invention.
Figure 6:
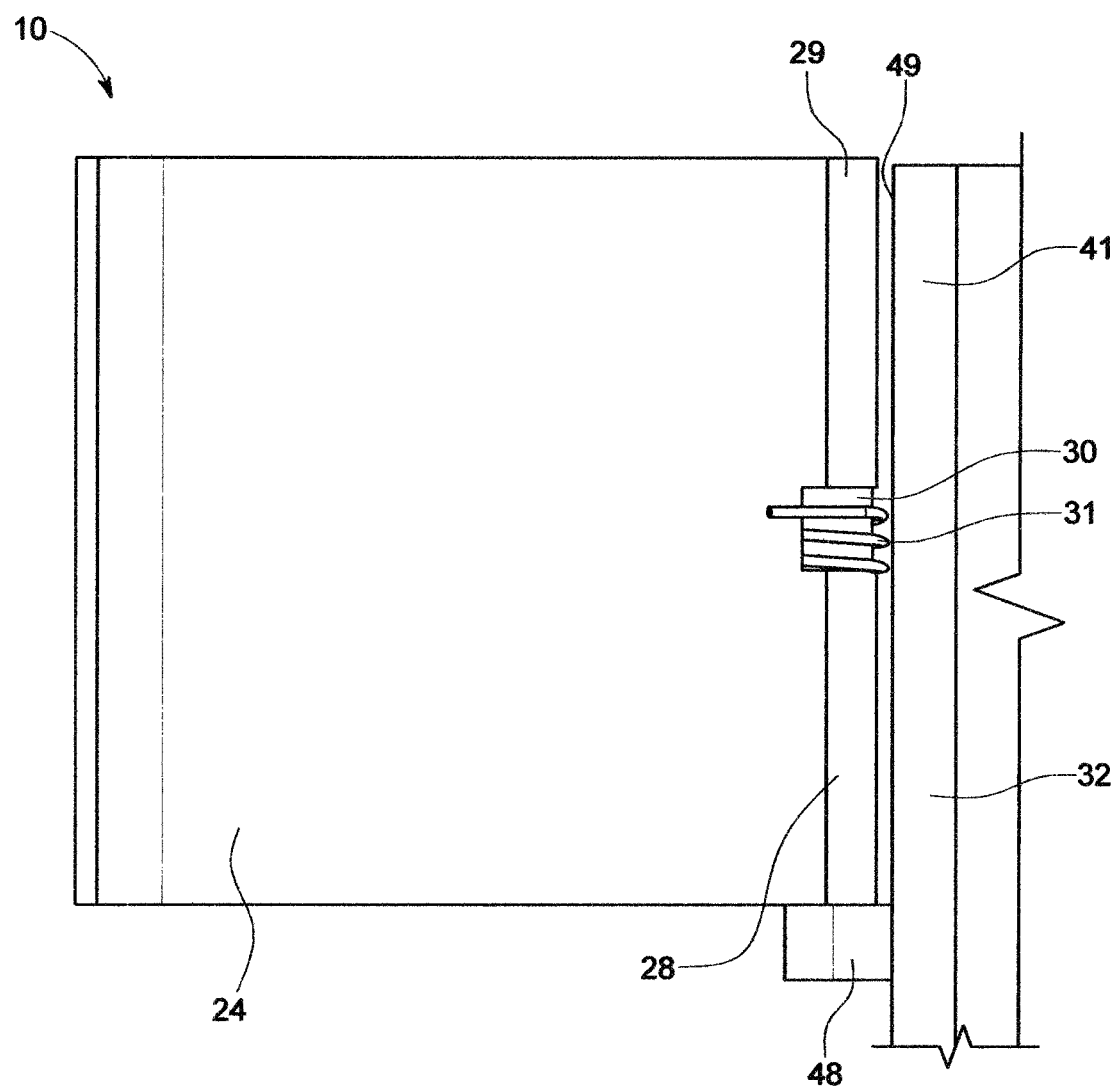
FIG. 6 is a side elevation view of the fourth embodiment of the present invention.

As a fourth embodiment as illustrated in FIGS. 5 & 6, the plug holder 32 includes a pair of back walls 41, 44. Each of the back walls 41, 44 has a side edge 42, 45 with a recessed upper portion 43, 46. Each of the tubular connectors 28, 28 are disposed in the recessed portions 43, 46 and conventionally coupled to the side edge 42, 45 of a respective back wall 41, 44 with the back walls 41, 44 being pivotable for spreading the clamping members 24, 26 apart and clamping the clamping members 24, 26 about the pole 53.

In use, a user secures the securement assembly 11 about the IV pole 53 and then inserts the power plug 54 into the cavity 50 of the plug holder 32 before moving the IV pole 53 along a floor to prevent the power cord 55 and plug 54 from getting tangled up with the wheels on the IV pole 53.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the IV pole power plug support device. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An IV (intravenous) pole power plug support device comprising:
   a securement assembly adapted to be removably engaged about an IV pole; and
   a power plug holder in communication with the securement assembly, wherein the power plug holder has a back wall, opposed side walls extending from the back wall, a bottom wall having an opening disposed therethrough, a front wall having top and bottom edges and an opening disposed therethrough and through the top and bottom edges and being in fluid communication with the opening through the bottom wall for receiving a power cord therethrough, and also has a cavity disposed therein for holding a power plug, wherein the back wall, the opposed side walls, and the front wall are substantially planar walls, wherein the front wall has side edge portions which line the opening through the front wall and which are bowed outwardly to accommodate different shapes and sizes of the power plug held in the cavity, the front wall including two sections extending from respective side walls inward toward each other, the edge portions extending from respective front wall sections outward away from the back wall.

2. The IV pole power plug support device as described in claim 1, wherein the securement assembly is movably attached to the plug holder.

3. The IV pole power plug support device as described in claim 2, wherein the securement assembly also includes a pair of extensions extending outwardly from the power plug holder to form a pole receiving and engaging slot therebetween.

4. The IV pole power plug support device as described in claim 3, wherein each of the extensions has a main portion and an end portion, wherein the main portions are laterally curved towards each other and the end portions are angled away from each other.

5. The IV pole power plug support device as described in claim 1, wherein the securement assembly includes a pair of clamping members spaced apart with each having a length and a proximate end edge for engaging about the IV pole.

6. The IV pole power plug support device as described in claim 5, wherein the securement assembly also includes tubular connectors each of which is coupled to the proximate end edge of a respective said clamping member.

7. The IV pole power plug support device as described in claim 6, wherein the clamping members are longitudinally curved towards one another.

8. The IV pole power plug support device as described in claim 7, wherein the securement assembly further includes a pin disposed through the tubular connectors and also includes a biased element disposed about the pin and engaged to the tubular connectors to engagably bias and secure the clamping members about the pole.

9. The IV pole power plug support device as described in claim 8, wherein the tubular connectors are hollow and each have a longitudinal axis which is arranged parallel to the proximate end edge of a respective said clamping member.

10. The IV pole power plug support device as described in claim 8, wherein the plug holder includes a back wall having a back side.

11. The IV pole power plug support device as described in claim 10, wherein the plug holder also includes support members spaced apart and integral to the back side of the back wall with the pin being disposed in the support members to interconnect the clamping members to the plug holder.

12. The IV pole power plug support device as described in claim 11, wherein the tubular connectors are disposed between and are longitudinally aligned with the support members.

13. The IV pole power plug support device as described in claim 8, wherein the plug holder includes a pair of back walls.

14. The IV pole power plug support device as described in claim 13, wherein each of the back walls has a side edge with a recessed upper portion.

15. The IV pole power plug support device as described in claim 14, wherein each of the tubular connectors are disposed in the recessed portions and coupled to the side edge of a respective said back wall with the back walls being pivotable for spreading the clamping members apart and clamping the clamping members about the pole.

16. An IV (intravenous) pole power plug support device comprising:
a securement assembly adapted to be removably engaged about an IV pole; and
a power plug holder in communication with the securement assembly, wherein the securement assembly includes a pair of clamping members spaced apart with each having a length and a proximate end edge for engaging about the IV pole, wherein the securement assembly also includes tubular connectors each of which is coupled to the proximate end edge of a respective said clamping member, wherein the securement assembly further includes a pin disposed through the tubular connectors and also includes a biased element disposed about the pin and engaged to the tubular connectors to engagably bias and secure the clamping members about the pole, wherein the plug holder includes a back wall having a back side, and wherein the plug holder also includes support members spaced apart and integral to the back side of the back wall with the pin being disposed in the support members to interconnect the clamping members to the plug holder.

17. The IV pole power plug support device as described in claim 16, wherein the tubular connectors are disposed between and are longitudinally aligned with the support members.

18. An IV (intravenous) pole power plug support device comprising:
a securement assembly adapted to be removably engaged about an IV pole; and
a power plug holder in communication with the securement assembly, wherein the securement assembly includes a pair of clamping members spaced apart with each having a length and a proximate end edge for engaging about the IV pole, wherein the securement assembly also includes tubular connectors each of which is coupled to the proximate end edge of a respective said clamping member, wherein the securement assembly further includes a pin disposed through the tubular connectors and also includes a biased element disposed about the pin and engaged to the tubular connectors to engagably bias and secure the clamping members about the pole, wherein the plug holder includes a pair of back walls, wherein each of the back walls has a side edge with a recessed upper portion, and wherein each of the tubular connectors are disposed in the recessed portions and coupled to the side edge of a respective said back wall with the back walls being pivotable for spreading the clamping members apart and clamping the clamping members about the pole.

* * * * *